(12) United States Patent
Müller-Pathle

(10) Patent No.: US 9,649,435 B2
(45) Date of Patent: May 16, 2017

(54) DOSING MECHANISM

(75) Inventor: Stephan Müller-Pathle, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 493 days.

(21) Appl. No.: 14/007,556

(22) PCT Filed: Mar. 28, 2012

(86) PCT No.: PCT/EP2012/055558
§ 371 (c)(1),
(2), (4) Date: Sep. 25, 2013

(87) PCT Pub. No.: WO2012/130903
PCT Pub. Date: Oct. 4, 2012

(65) Prior Publication Data
US 2014/0018730 A1    Jan. 16, 2014

(30) Foreign Application Priority Data

Mar. 31, 2011  (EP) .................................... 11160653

(51) Int. Cl.
*A61M 5/00* (2006.01)
*A61M 5/168* (2006.01)
*A61M 5/315* (2006.01)

(52) U.S. Cl.
CPC .... *A61M 5/16809* (2013.01); *A61M 5/16804* (2013.01); *A61M 5/16877* (2013.01); *A61M 5/31525* (2013.01)

(58) Field of Classification Search
CPC .......... A61M 5/16809; A61M 5/31525; A61M 5/1422
See application file for complete search history.

(56) References Cited

U.S. PATENT DOCUMENTS 4,838,860 A * 6/1989 Groshong ........... A61M 5/1422
128/DIG. 12
5,547,110 A    8/1996 Keller et al.
(Continued)

FOREIGN PATENT DOCUMENTS

CN    101132819 A    2/2008
EP    1634612 A1    3/2006
(Continued)

OTHER PUBLICATIONS

English Translation of First Office Action issued in Chinese Patent Application No. 201280021126.6 dated Mar. 26, 2015.

*Primary Examiner* — Emily Schmidt
(74) *Attorney, Agent, or Firm* — McDonnell Boehnen Hulbert & Berghoff LLP

(57) ABSTRACT

The invention relates to a dosing mechanism for a fluid, comprising an inlet, an outlet, a dosing pipe and two valve groups with an inlet valve and an outlet valve each, wherein the inlet is connected to both inlet valves and the outlet is connected to both outlet valves, wherein the inlet valve of one group is arranged to connect the inlet to a first end of the dosing pipe while the outlet valve of the same group is arranged to connect the outlet to a second end of the dosing pipe, wherein the inlet valve of the other group is arranged to connect the inlet to the second end of the dosing pipe while the outlet valve of the same group is arranged to connect the outlet to the first end of the dosing pipe, wherein control means are arranged to open only the valves of one group at a time thereby allowing the fluid to flow from the inlet through the dosing pipe to the outlet, wherein a dosing object is arranged in the dosing pipe in a manner to be translated from one end towards the other by the fluid, wherein a dose to be delivered from the output is determinable by a position of the dosing object in the dosing pipe.

10 Claims, 1 Drawing Sheet

(56) References Cited

U.S. PATENT DOCUMENTS

| | | | |
|---|---|---|---|
| 5,807,321 A | 9/1998 | Stoker et al. | |
| 6,179,583 B1 * | 1/2001 | Weston | A61M 5/16809 |
| | | | 222/334 |
| 2003/0229310 A1 | 12/2003 | Flaherty et al. | |
| 2006/0084921 A1 | 4/2006 | Darnell | |
| 2008/0086111 A1 * | 4/2008 | Cowan | A61M 5/14216 |
| | | | 604/522 |
| 2010/0114059 A1 * | 5/2010 | Hiniduma-Lokuge | A61M 5/1452 |
| | | | 604/500 |

FOREIGN PATENT DOCUMENTS

| | | |
|---|---|---|
| WO | 2006032070 A1 | 3/2006 |
| WO | 2006044029 A2 | 4/2006 |
| WO | 2008094672 A2 | 8/2008 |

* cited by examiner

DOSING MECHANISM

CROSS REFERENCE TO RELATED APPLICATIONS

The present application is a U.S. National Phase Application pursuant to 35 U.S.C. §371 of International Application No. PCT/EP2012/055558 filed Mar. 28, 2012, which claims priority to European Patent Application No. 11160653.9 filed Mar. 31, 2011. The entire disclosure contents of these applications are herewith incorporated by reference into the present application.

FIELD OF INVENTION

The invention relates to a dosing mechanism for a fluid.

BACKGROUND

Medical injection systems such as pen injectors are supposed to allow patients to self-administer required doses of medicaments, such as insulin. When injecting medicaments, dose accuracy is of therapeutic relevance. Conventional injection systems comprise a carpule, e.g. filled with insulin. A stopper is arranged in the carpule in a manner to be translated by a dosing mechanism of the pen injector by a distance corresponding to the required dose thus displacing the dose from the carpule through an injection needle into the injection site, e.g. the patient's skin. Dose accuracy in such systems depends on the precision of the translation of the stopper, tolerances in the internal diameter of the carpule and the compressibility of the stopper.

WO 2006/032070 A1 discloses a device for the dosed intake and delivery of a liquid, especially an infusion liquid. Said device comprises a cylinder embodying a liquid chamber that can be pressurised, a piston which is guided in the cylinder along the cylinder axis, and at least one line for introducing liquid into the liquid chamber and for dispensing liquid from the same. The aim of the invention is to ensure that the device is easy to handle and to prevent the risk of contamination of the infusion solution as far as possible. To this end, the piston can be displaced in the cylinder, against an elastic force, from an idle position defined by an abutment, to an end position defined by an abutment, in order to displace a defined cylinder volume.

SUMMARY

It is an object of the present invention to provide an improved dosing mechanism for a fluid.

The object is achieved by a dosing mechanism according to claim 1.

Preferred embodiments of the invention are given in the dependent claims.

A dosing mechanism for a fluid according to the invention comprises an inlet, an outlet, a dosing pipe and two valve groups with an inlet valve and an outlet valve each. The inlet is connected to both inlet valves and the outlet is connected to both outlet valves, wherein the inlet valve of one group is arranged to connect the inlet to a first end of the dosing pipe while the outlet valve of the same group is arranged to connect the outlet to a second end of the dosing pipe. The inlet valve of the other group is arranged to connect the inlet to the second end of the dosing pipe while the outlet valve of the same group is arranged to connect the outlet to the first end of the dosing pipe. Control means are arranged to open only the valves of one group at a time thereby allowing the fluid to flow from the inlet through the dosing pipe to the outlet. A dosing object is arranged in the dosing pipe in a manner to be translated from one end towards the other by the flowing fluid, wherein a dose to be delivered from the output is determinable by a position of the dosing object in the dosing pipe. If one group of valves is opened and the fluid at the inlet is under pressure the fluid flows from the inlet through the open inlet valve, the dosing pipe and the open outlet valve to the outlet thereby taking the dosing object with it and moving it from one end of the dosing pipe towards the other. The distance travelled by the dosing object between two positions correlates with the dose volume delivered through the outlet. If the dosing object has bottomed out at one end the open valves may be closed. By opening the valves of the other group, another dose may be delivered while the dosing object is moved in the opposite direction by the fluid.

In one embodiment the dosing object may be arranged as a ball, wherein the ends of the dosing pipe are arranged as seal seats so that the ball, when reaching one of the ends during translation by the flowing fluid, seals the dosing pipe thus preventing further delivery with the respective current group of valves open. In order to deliver another dose the currently open valves have to be closed and the valves of the other group have to be opened. The fluid flowing through the dosing pipe in the other direction will take the ball with it until it bottoms out at the other end sealing it. The volume of the dosing pipe less the ball may be chosen to represent a dose unit of the fluid to be delivered. Hence, when one group of valves is opened with the inlet under pressure exactly one unit of the fluid is delivered. In an example embodiment, the so defined dose unit is the same as an insulin unit. Alternatively, an integer n (n=1, 2, 3, . . . k) multiple of the so defined dose unit is an insulin unit. Thus, n activations of the pump mechanism result in the dosing object pumping an equivalent of one insulin unit.

In order to seal the ends by the ball the ends of the dosing pipe may be tapered.

The dosing object may also have a different shape such as a stopper. The stopper may comprise an elastic material such as rubber and seals against the walls of the dosing pipe, wherein the end of the dosing pipe may have a reduced inner diameter in order to form a seal seat.

In another embodiment a sensor may be arranged for determining the position of the dosing object within the dosing pipe, the sensor connected to the control means, e.g. a microprocessor. The control means is arranged to open and close the valves depending on a distance travelled by the dosing object between two positions which may be detected by the sensor and depending on a set dose volume to be delivered. In this embodiment the dose volume may be smaller than the volume of the dosing pipe less the dosing object. If a dose greater than the volume of the dosing pipe less the dosing object shall be delivered the control means has to switch to the other group of valves at the latest when the dosing object has bottomed out at one end of the dosing pipe. Application of such a sensor allows for improving the reliability of the dosing mechanism since malfunctions such as clogged injection needles may be detected if the dosing object does not or insufficiently move.

The sensor may be arranged as a linear charge coupled device, wherein the dosing pipe is transparent for allowing optical detection of the dosing object's position. Preferably a light source would be arranged to illuminate the dosing object in such a manner that the sensor is subjected to transmitted light.

The dosing object may be a ball or a stopper or another suitable object. Note that the dosing object does not necessarily have to seal the end of the dosing tube in this embodiment when having bottomed out.

In another embodiment the dosing object may be an air bubble. The sensor is arranged to detect the air bubble and the control means may be arranged to prevent injecting air by proper controlling of the valves. When applied in very small dosing pipes the air bubble itself can act as a seal. If the dosing pipe inner diameter is very small a significant pressure is needed to get the air bubble through.

The small diameter of the dosing pipe with the surface tension of the fluid prevent the air bubble moving by buoyancy.

The dosing mechanism may be applied in an injection device for delivering a liquid drug, comprising a drug container and displacement means for displacing the drug from the container through a container outlet. The container outlet is connected to the inlet of the dosing mechanism, wherein the outlet of the dosing mechanism is connected to a nozzle, such as an injection needle or a jet injector.

A stopper may be arranged in the drug container for displacing the drug on translation into the drug container driven by a drive spring. The stopper may be under permanent load from the drive spring. Delivery of the drug is controlled by the control unit opening one respective group of valves.

Other container designs may also be used such as deformable bags compressed by rolls or other compression means.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
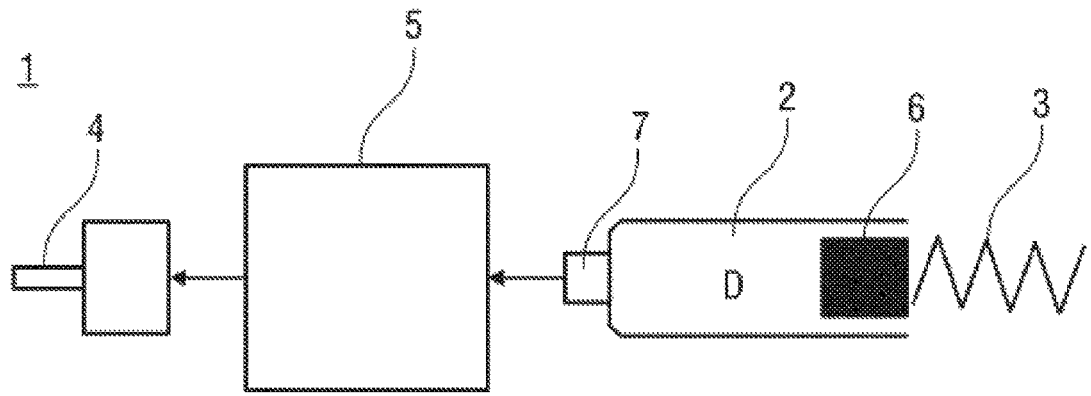
FIG. 1 is a schematic view of an injection device with a drug container, a drive spring, an injection needle and a dosing mechanism.

FIG. 1 shows a schematic view of an injection device 1 with a drug container 2, a drive spring 3, an injection needle 4 and a dosing mechanism 5. The drive spring 3 acts on a stopper 6 disposed within the drug container 2 and translatable in a manner to displace drug D stored in the drug container 2 through a container outlet 7. The container outlet 7 is connected to an inlet of the dosing mechanism 5, wherein an outlet of the dosing mechanism 5 is connected to the injection needle 4. The stopper 6 is under permanent load from the drive spring 3 so delivery of the drug D through the needle 4 is controlled by the dosing mechanism 5 only.

Figure 2:
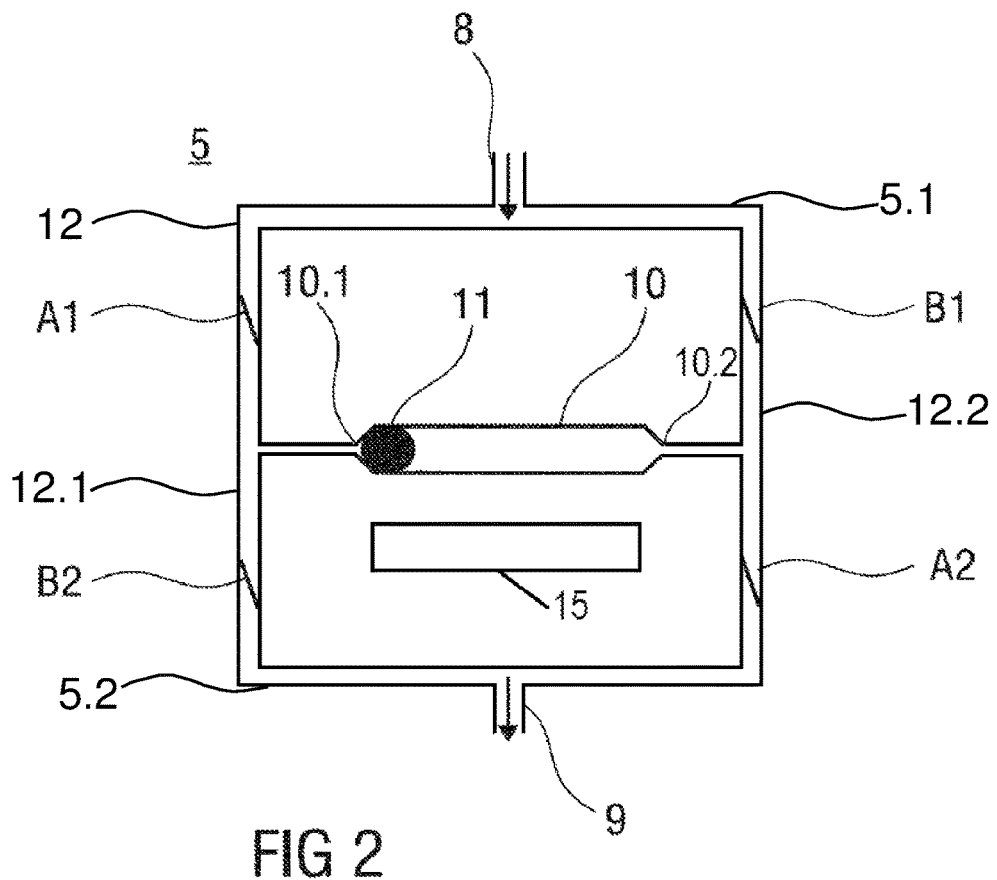
FIG. 2 is a schematic view of the dosing mechanism with a dosing object within a dosing tube, two inlet valves and two outlet valves.

FIG. 2 shows a schematic view of the dosing mechanism 5.

The dosing mechanism 5 comprises an inlet 8 located at a first end 5.1 of the dosing mechanism 5, an outlet 9 located at a second end 5.2 of the dosing mechanism 5, a dosing pipe 10 and two valve groups A, B with an inlet valve A1, B1 and an outlet valve A2, B2 each. The inlet 8 is connected to both inlet valves A1, B1 and the outlet 9 is connected to both outlet valves A2, B2. The inlet valve A1 of group A is arranged to connect the inlet 8 to a first end 10.1 of the dosing pipe 10 while the outlet valve A2 of the same group A is arranged to connect the outlet 9 to a second end 10.2 of the dosing pipe 10. The inlet valve B1 of the other group B is arranged to connect the inlet 8 to the second end 10.2 of the dosing pipe 10 while the outlet valve B2 of the same group B is arranged to connect the outlet 9 to the first end 10.1 of the dosing pipe 10. Control means (not illustrated) are arranged to open only the valves A1, A2, B1, B2 of one group A, B at a time thereby allowing the drug D to flow from the inlet 8 through the dosing pipe 10 to the outlet 9. A dosing object 11 is arranged in the dosing pipe 10 in a manner to be translated from one end 10.1, 10.2 towards the other end 10.2, 10.1 by the flowing drug D, wherein a dose to be delivered from the output 9 is determinable by a position of the dosing object 11 in the dosing pipe 10. If one group A, B of valves A1, A2, B1, B2 is opened and the drug D at the inlet 8 is under pressure the drug D flows from the inlet 8 through the open inlet valve A1, B1, the dosing pipe 10 and the respective open outlet valve A2, B2 to the outlet 9 thereby taking the dosing object 11 with it and moving it from one end 10.1, 10.2 of the dosing pipe 10 towards the other 10.2, 10.1. The distance travelled by the dosing object 11 between two positions correlates with the dose volume delivered through the outlet 9. If the dosing object 11 has bottomed out at one end 10.2, 10.1 the open valves A1, A2, B1, B2 may be closed. By opening the valves B1, B2, A1, A2 of the other group B, A, another dose may be delivered while the dosing object 11 is moved in the opposite direction by the drug.

In the illustrated embodiment the dosing object 11 is arranged as a ball, wherein the ends 10.1, 10.2 of the dosing pipe 10 are tapered so that the dosing object 11, when reaching one of the ends 10.1, 10.2 during translation by the flowing drug D, seals the dosing pipe 10 thus preventing further delivery with the respective current group B, A of open valves B1, B2, A1, A2. In order to deliver another dose the currently open valves B1, B2, A1, A2 have to be closed and the valves A1, A2, B1, B2 of the other group A, B have to be opened. The drug D flowing through the dosing pipe 10 in the other direction will take the dosing object 11 with it until it bottoms out at the other end 10.2, 10.1 sealing it. The volume of the dosing pipe 10 less the dosing object 11 may be chosen to represent a dose unit of the drug D to be delivered. Hence, when one group A, B of valves A1, A2, B1, B2 is opened with the inlet 8 under pressure exactly one unit of the drug D is delivered.

The dosing object 11 may also seal against the dosing pipe 10 walls to ensure dose accuracy. For this purpose the dosing object 11, e.g. the ball or a stopper made of an elastic material such as rubber may exactly fit into the dosing pipe 10.

In order to reduce dead volume in front of the dosing object 11, the connection from the ends 10.1, 10.2 to the branch pipe 12 towards the valves A1, B2 disposed in a first branch 12.1 of the branch pipe 12 and A2, B1 disposed in a second branch 12.2 of the branch pipe 12 has to be short.

In an alternative embodiment a sensor 15 may be arranged for determining the position of the dosing object 11 within the dosing pipe 10, the sensor 15 connected to the control means, e.g. a microprocessor. The control means is arranged to open and close the valves A1, A2, B1, B2 depending on a distance travelled by the dosing object 11 between two positions which may be detected by the sensor 15 and depending on a set dose volume to be delivered.

The sensor may be arranged as a linear charge coupled device, wherein the dosing pipe 10 is transparent for allowing optical detection of the dosing object's 11 position. Preferably a light source would be arranged to illuminate the dosing object 11 in such a manner that the sensor is subjected to transmitted or reflected light.

The dosing object 11 may be a ball or a stopper or another suitable object, such as an air bubble.

Other container 2 designs may also be used such as deformable bags compressed by rolls or other compression means.

The dosing mechanism 5 may be applied in other medical or non-medical contexts.

The invention claimed is:

1. Dosing mechanism for a fluid, comprising an inlet, an outlet, a dosing pipe and a first valve group and a second valve group each having an inlet valve and an outlet valve, wherein the inlet is connected to both inlet valves and the outlet is connected to both outlet valves, wherein the inlet valve of the first valve group is arranged to connect the inlet to a first end of the dosing pipe while the outlet valve of the first valve group is arranged to connect the outlet to a second end of the dosing pipe, wherein the inlet valve of the second valve group is arranged to connect the inlet to the second end of the dosing pipe while the outlet valve of the second valve group is arranged to connect the outlet to the first end of the dosing pipe, wherein the first valve group and the second valve group are configured such that only the valves of one of the first or second valve group are open at a time thereby allowing the fluid to flow from the inlet through the dosing pipe to the outlet, wherein a dosing object is arranged in the dosing pipe in a manner to be translated from one end of the dosing pipe towards the other by the fluid, wherein the inlet and the outlet are arranged on opposing sides of the dosing pipe, wherein a sensor is arranged for determining the position of the dosing object within the dosing pipe and configured to open and close the first valve group and the second valve group depending on (i) a distance travelled by the dosing object between two positions detected by the sensor and (ii) a set dose volume to be delivered, so as to allow delivery of a dose volume from the dosing pipe smaller than the volume of the dosing pipe less the dosing object, wherein the sensor is a linear charge coupled device, and wherein the dosing pipe is transparent.

2. Dosing mechanism according to claim 1, wherein a distance travelled by the dosing object between two positions correlates with the dose volume delivered through the outlet.

3. Dosing mechanism according to claim 1, wherein the dosing object is a ball, wherein the ends of the dosing pipe are seal seats so that the ball, when reaching one of the ends during translation seals the dosing pipe preventing further delivery.

4. Dosing mechanism according to claim 3, wherein the ends of the dosing pipe are tapered or have a reduced diameter.

5. Dosing mechanism according to claim 1, wherein the dosing object is a stopper comprising an elastic material, wherein the ends of the dosing pipe are seal seats so that the stopper, when reaching one of the ends during translation seals the dosing pipe preventing further delivery.

6. Dosing mechanism according to claim 1, the dosing object is a ball or a stopper.

7. Dosing mechanism according to claim 1, wherein the dosing object is an air bubble.

8. Injection device for delivering a liquid drug, comprising a drug container, displacement mechanism for displacing the drug from the container through a container outlet, wherein the container outlet is connected to the inlet of the dosing mechanism according to claim 1, wherein the outlet of the dosing mechanism is connected to a nozzle is an injection needle.

9. Injection device according to claim 8, wherein the displacement mechanism is a stopper and is arranged in the drug container for displacing the drug on translation into the drug container driven by a drive spring.

10. Dosing mechanism for a fluid, comprising an inlet, an outlet, a dosing pipe and a first valve group and a second valve group each having an inlet valve and an outlet valve, wherein the inlet is connected to both inlet valves and the outlet is connected to both outlet valves, wherein the inlet valve of the first valve group is arranged to connect the inlet to a first end of the dosing pipe while the outlet valve of the first valve group is arranged to connect the outlet to a second end of the dosing pipe, wherein the inlet valve of the second valve group is arranged to connect the inlet to the second end of the dosing pipe while the outlet valve of the second valve group is arranged to connect the outlet to the first end of the dosing pipe, wherein the first valve group and the second valve group are configured such that only the valves of one of the first or second valve group are open at a time thereby allowing the fluid to flow from the inlet through the dosing pipe to the outlet, wherein a dosing object is arranged in the dosing pipe in a manner to be translated from one end of the dosing pipe towards the other by the fluid, wherein the inlet and the outlet are arranged on opposing sides of the dosing pipe, wherein a sensor is arranged for determining the position of the dosing object within the dosing pipe and configured to open and close the first valve group and the second valve group depending on (i) a distance travelled by the dosing object between two positions detected by the sensor and (ii) a set dose volume to be delivered, so as to allow delivery of a dose volume from the dosing pipe smaller than the volume of the dosing pipe less the dosing object.

* * * * *